(12) United States Patent
Chen et al.

(10) Patent No.: US 11,598,741 B2
(45) Date of Patent: Mar. 7, 2023

(54) TUNGSTEN TRIOXIDE/SILICON NANOCOMPOSITE STRUCTURE, METHOD FOR MANUFACTURING THE SAME AND GAS SENSING DEVICE HAVING THE SAME

(71) Applicant: National Cheng Kung University, Tainan (TW)

(72) Inventors: Chia-Yun Chen, Tainan (TW); Po-Hsuan Hsiao, Tainan (TW); Pin-Ju Chien, Kaohsiung (TW)

(73) Assignee: National Cheng Kung University, Tainan (TW)

( * ) Notice: Subject to any disclaimer, the term of this patent is extended or adjusted under 35 U.S.C. 154(b) by 227 days.

(21) Appl. No.: 17/123,054

(22) Filed: Dec. 15, 2020

(65) Prior Publication Data

US 2022/0163472 A1 May 26, 2022

(30) Foreign Application Priority Data

Nov. 23, 2020 (TW) .................... 109140955

(51) Int. Cl.
*G01N 27/12* (2006.01)
*C01B 33/02* (2006.01)
*C01G 41/02* (2006.01)
*G01N 33/00* (2006.01)

(52) U.S. Cl.
CPC .......... *G01N 27/127* (2013.01); *C01B 33/02* (2013.01); *C01G 41/02* (2013.01); *G01N 27/128* (2013.01); *G01N 33/0037* (2013.01); *C01P 2004/03* (2013.01); *C01P 2004/16* (2013.01); *C01P 2004/64* (2013.01)

(58) Field of Classification Search
None
See application file for complete search history.

(56) References Cited

U.S. PATENT DOCUMENTS

2003/0099575 A1* 5/2003 Sung ................ G01N 33/0044
422/98

FOREIGN PATENT DOCUMENTS

| CN | 101799443 A | 8/2010 |
| CN | 103626117 A | 3/2014 |
| CN | 103630572 A | 3/2014 |
| CN | 110511059 | * 11/2019 |

OTHER PUBLICATIONS

English translation of CN 110511059 (Year: 2019).*

* cited by examiner

*Primary Examiner* — Jeffrey D Washville
(74) *Attorney, Agent, or Firm* — Winston Hsu

(57) ABSTRACT

A method for manufacturing a tungsten trioxide/silicon nanocomposite structure includes steps as follows. A silicon substrate is provided, wherein a surface of the silicon substrate is formed with a plurality of microstructures. A tungsten trioxide precursor solution is provided, wherein the tungsten trioxide precursor solution is contacted with the silicon substrate. A hydrothermal synthesis step is conducted, wherein the tungsten trioxide precursor solution is reacted to form a plurality of tungsten trioxide particles on the plurality of microstructures, so as to obtain the tungsten trioxide/silicon nanocomposite structure.

19 Claims, 6 Drawing Sheets

TUNGSTEN TRIOXIDE/SILICON NANOCOMPOSITE STRUCTURE, METHOD FOR MANUFACTURING THE SAME AND GAS SENSING DEVICE HAVING THE SAME

BACKGROUND OF THE INVENTION

1. Field of the Invention

The present disclosure relates to a tungsten trioxide ($WO_3$)/silicon (Si) nanocomposite structure, a method for manufacturing the same and a gas sensing device having the same, and more particularly, to a low-cost $WO_3$/Si nanocomposite structure, a method for manufacturing the same and a gas sensing device having the same.

2. Description of the Prior Art

Air pollution refers to the presence of at least one air pollutant in the atmosphere, and the concentration of the air pollutant is sufficient to affect the health of humans, animals, and plants for a duration. Take nitrogen oxides ($NO_x$) as an example. $NO_x$ is a common air pollutant. $NO_x$ includes gases such as nitric oxide (NO) and nitrogen dioxide ($NO_2$), which are the main components of acid rain and may generate volatile substances causing human respiratory diseases by catalyzation of sunlight. $NO_x$ bring negative effects on the environment and human health. Therefore, how to monitor the concentration of air pollutants has attracted much attention recently.

Metal oxide semiconductor materials refer to metal oxides, such as zinc oxide (ZnO), tin oxide ($SnO_2$) and $WO_3$, which have semiconductor characteristics due to structural defects. When gas molecules adsorb on the surface of the metal oxide semiconductor material, the conductivity will change. Therefore, the concentration of gas molecules can be deduced by measuring the change of resistance. Accordingly, the metal oxide semiconductor materials are widely applied to gas sensing device. Most of the commercially available gas sensing devices using the metal oxide semiconductor materials form the sensing film by depositing metal oxide particles on a substrate through sputtering method. However, in the sputtering method, it requires an electric field to generate high-energy accelerated particles to bombard the target material in a vacuum state. Accordingly, the threshold of the apparatus is high, which leads to high costs.

SUMMARY OF THE INVENTION

According to one embodiment of the present disclosure, a method for manufacturing a $WO_3$/Si nanocomposite structure includes steps as follows. A silicon substrate is provided, wherein a surface of the silicon substrate is formed with a plurality of microstructures. A $WO_3$ precursor solution is provided, wherein the $WO_3$ precursor solution is contacted with the silicon substrate. A hydrothermal synthesis step is conducted, wherein the $WO_3$ precursor solution is reacted to form a plurality of $WO_3$ particles on the plurality of microstructures, so as to obtain the $WO_3$/Si nanocomposite structure.

According to another embodiment of the present disclosure, a $WO_3$/Si nanocomposite structure is provided. The $WO_3$/Si nanocomposite structure is manufactured by the aforementioned method.

According to yet another embodiment of the present disclosure, a gas sensing device is provided. The gas sensing device includes the aforementioned $WO_3$/Si nanocomposite structure.

These and other objectives of the present invention will no doubt become obvious to those of ordinary skill in the art after reading the following detailed description of the preferred embodiment that is illustrated in the various figures and drawings.

DETAILED DESCRIPTION

<Method for Manufacturing $WO_3$/Si Nanocomposite Structure>

Figure 1:
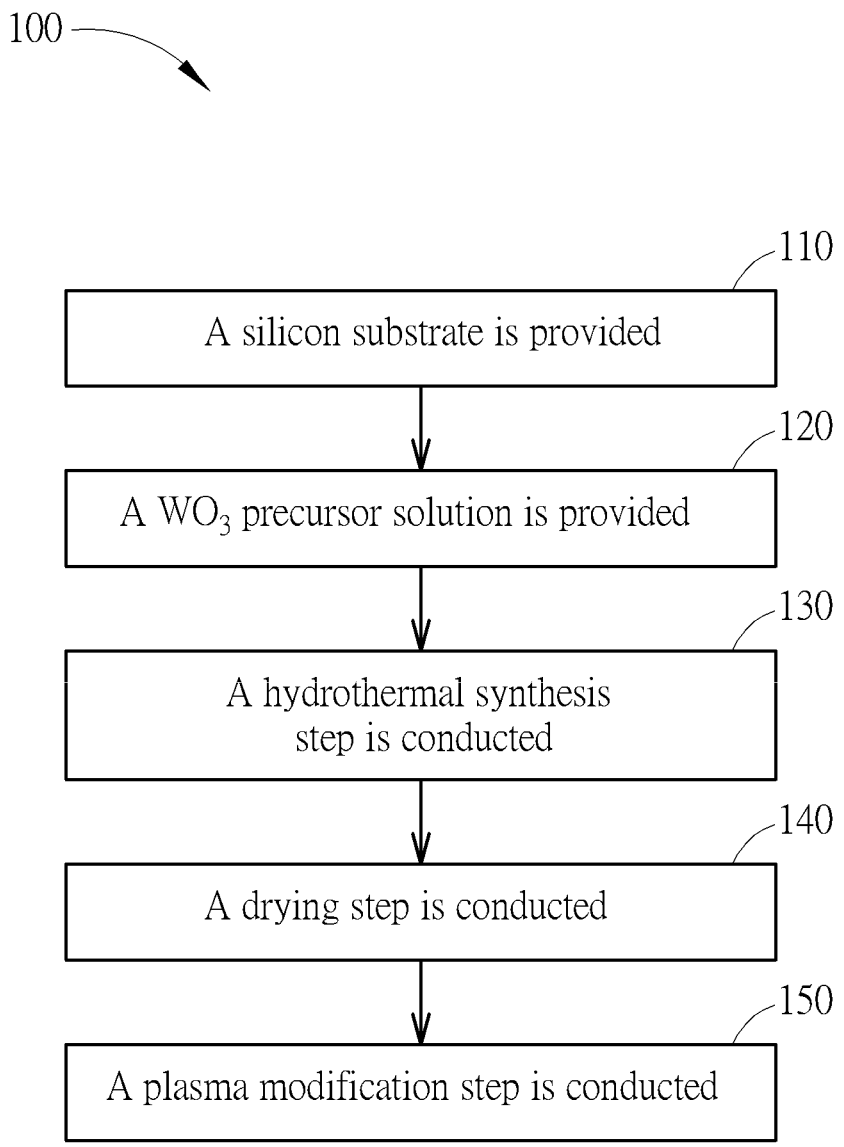
FIG. 1 is a flow diagram of a method for manufacturing a $WO_3$/Si nanocomposite structure according to one embodiment of the present disclosure.

Please refer to FIG. 1, which is a flow diagram of a method 100 for manufacturing a $WO_3$/Si nanocomposite structure according to one embodiment of the present disclosure. In FIG. 1, the method 100 for manufacturing the $WO_3$/Si nanocomposite structure includes Step 110 to Step 130, and can selectively include Step 140 and Step 150. In Step 110, a silicon substrate is provided, wherein a surface of the silicon substrate is formed with a plurality of microstructures. Specifically, the silicon substrate can be monocrystalline silicon, and can optionally be doped with other elements, such as group IIIA elements or group VA elements. That is, the silicon substrate can be a p-type silicon substrate or an n-type silicon substrate.

Figure 2:
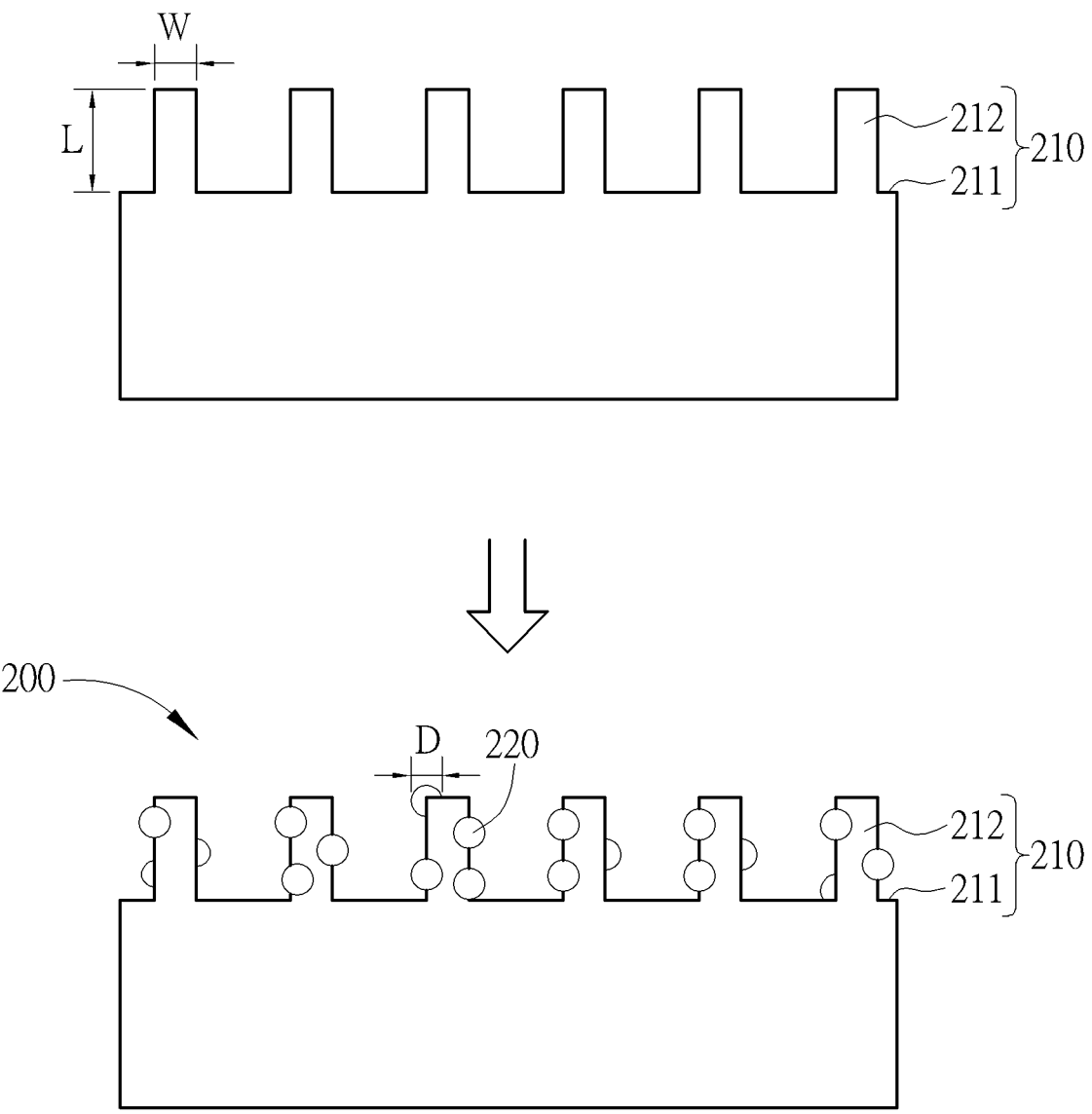
FIG. 2 is a schematic diagram showing a silicon substrate transformed into the $WO_3$/Si nanocomposite structure via a hydrothermal synthesis step.

Please refer to FIG. 2, which is a schematic diagram showing a silicon substrate 210 transformed into a $WO_3$/Si nanocomposite structure 200 via a hydrothermal synthesis step. As shown in FIG. 2, a surface 211 of the silicon substrate 210 is formed with a plurality of microstructures 212. Herein, each of the microstructures 212 is a straight nanowire, which is only exemplary, and the present disclosure is not limited thereto. The microstructures 212 are for increasing the surface area of the surface 211. Therefore, in other embodiments, the microstructures 212 can be arranged as curved nanowires, holes or other structures which can also increase the surface area of the surface 211. In FIG. 2, a length L of the nanowire can range from 400 nm to 1400 nm, and a width W of the nanowire can range from 40 nm to 500 nm. As such, it is favorable for enhancing the gas response. Preferably, the length L of the nanowire can range from 800 nm to 1200 nm, and the width W of the nanowire can range from 100 nm to 200 nm. For example, the silicon substrate 210 can be manufactured by a metal-assisted chemical etching process. That is, a silicon wafer with a smooth surface (without microstructures) is provided, and then the silicon wafer is etched by the metal-assisted chemical etching process to obtain the silicon substrate 210 having the surface 211 formed with the plurality of microstructures 212. How to form microstructures on the surface of the silicon wafer is well known and is not recited herein.

Referring back to FIG. 1, in Step 120, a $WO_3$ precursor solution is provided, wherein the $WO_3$ precursor solution is contacted with the silicon substrate.

Figure 3:
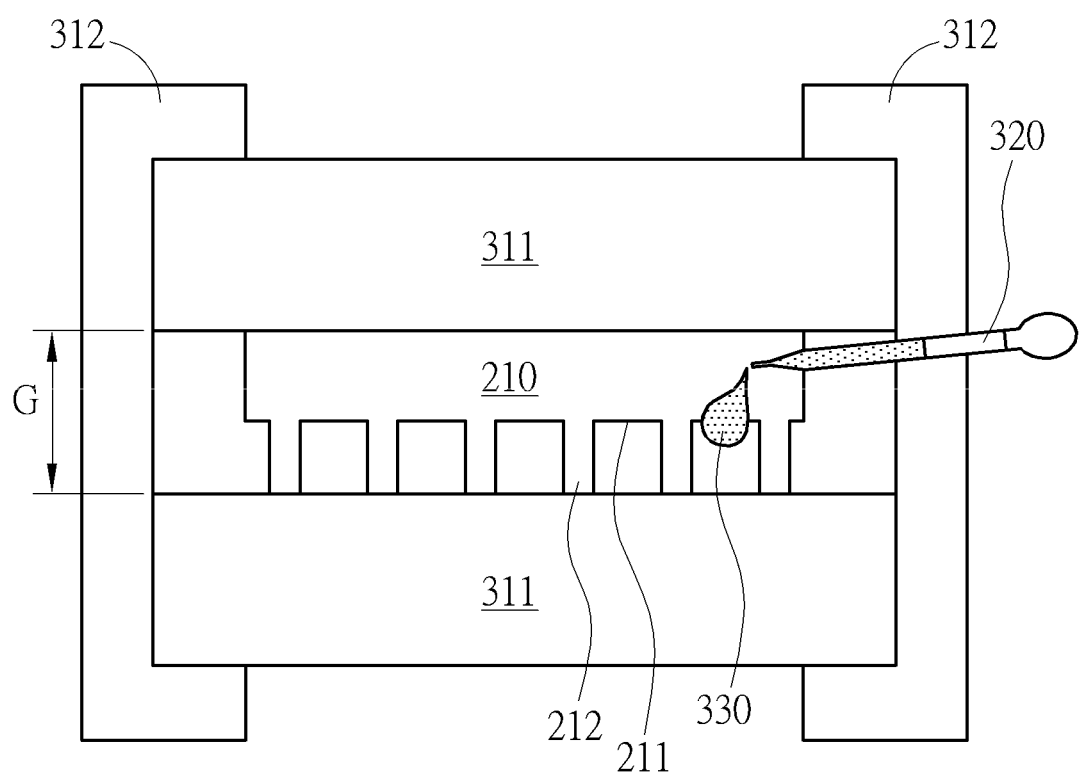
FIG. 3 is a top view showing a $WO_3$ precursor solution contacted with the silicon substrate according to one embodiment of the present disclosure.

Please refer to FIG. 3, which is a top view showing a $WO_3$ precursor solution 330 contacted with the silicon substrate 210 according to one embodiment. In FIG. 3, the silicon substrate 210 is disposed in a clamp device (reference numeral thereof is omitted). The clamp device includes two cover elements 311 and two clip elements 312. The silicon substrate 210 is disposed between the two cover elements 311, and the clip elements 312 clamp the two cover elements 311 to fix the silicon substrate 210 between the two cover elements 311. Herein, the number of the clip elements 312 is two, which is only exemplary, and the present disclosure is not limited thereto. The number of the clip elements 312 can be adjusted according to practical needs. A gap G is between the two cover elements 311, and the $WO_3$ precursor solution 330 can be dripped into the gap G between the two cover elements 311 to contact with the silicon substrate 210. Specifically, the cover elements 311 can be sheet structures and respectively disposed on two opposite sides of the silicon substrate 210 to sandwich the silicon substrate 210 therebetween. The clip elements 312 are configured to fix the two cover elements 311 and the silicon substrate 210, and provide the pressure required by the following hydrothermal synthesis step. In other words, the pressure of the silicon substrate 210 in the clamp device is greater than the atmospheric pressure. Furthermore, the clamping force provided by the clip elements 312 can be adjusted according to practical needs, so as to adjust the pressure of the silicon substrate 210 in the clamp device. The $WO_3$ precursor solution 330 can be contained in a dropper 320, and the $WO_3$ precursor solution 330 can be dripped into the gap G between the two cover elements 311 to contact with the silicon substrate 210 by using the dropper 320. By using the clamp device, it can prevent the $WO_3$ precursor solution from forming a film in the hydrothermal synthesis step and is favorable for $WO_3$ to be distributed on the microstructures 212 in the form of particles. As such, it is favorable for enhancing the gas response. By contacting the $WO_3$ precursor solution 330 with the silicon substrate 210 through dripping, it is favorable for the $WO_3$ precursor solution 330 to distribute evenly on the surface 211 of the silicon substrate 210 in a short time, and is favorable for controlling the total amount of the $WO_3$ precursor solution 330.

Figure 4:
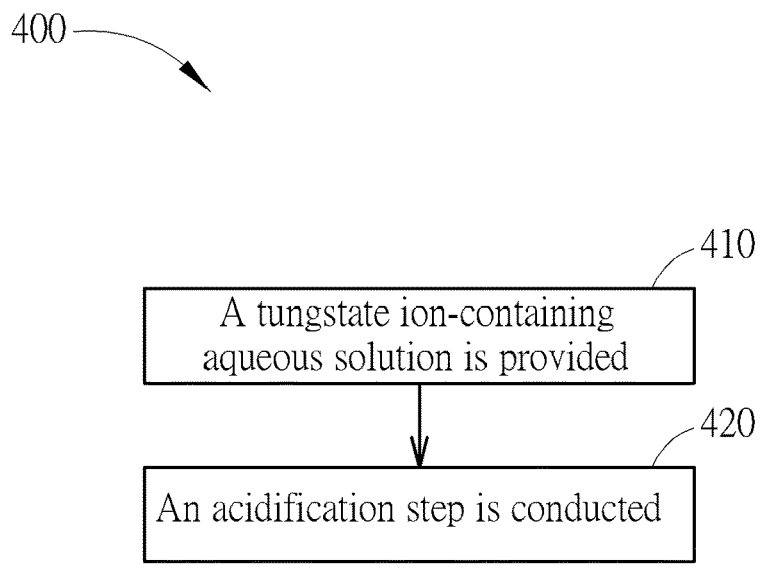
FIG. 4 is a flow diagram of a method for preparing the $WO_3$ precursor solution according to one embodiment of the present disclosure.

Please refer to FIG. 4, which is a flow diagram of a method 400 for preparing the $WO_3$ precursor solution according to one embodiment of the present disclosure. In FIG. 4, the method 400 for preparing the $WO_3$ precursor solution includes Step 410 and Step 420.

In Step 410, a tungstate ion-containing aqueous solution is provided, wherein the tungstate ion-containing aqueous solution includes tungstate ions ($WO_4^{2-}$) and water. The tungstate ion-containing aqueous solution can further include a dispersant for enhancing the dispersion of the tungstate ions in water, such that it can prevent the $WO_3$ particles from agglomerating. Accordingly, the dispersion of the $WO_3$ particles on the microstructures can be enhanced. A concentration of the tungstate ions in the tungstate ion-containing aqueous solution can range from 0.002 M to 1.8 M. A concentration of the dispersant in the tungstate ion-containing aqueous solution can range from 0.004 M to 0.4 M. According to one embodiment of the present disclosure, the tungstate ions can be provided by sodium tungstate ($Na_2WO_4$). For example, the tungstate ions can be obtained by dissolving $Na_2WO_4 \cdot 2H_2O$ in water. However, the present disclosure is not limited thereto. Substances which can be dissolved in water and can provide the tungstate ions can be used as the source providing the tungstate ions. The dispersant can be sodium chloride (NaCl). However, the present disclosure is not limited thereto. Substances which can be dissolved in water and do not react with the tungstate ions can be used as the dispersant.

In Step 420, an acidification step is conducted, wherein an acidic substance is added into the tungstate ion-containing aqueous solution to obtain the $WO_3$ precursor solution. The acidic substance is for adjusting the pH value, such that the pH value of the $WO_3$ precursor solution can be in a predetermined range, and the hydrogen ions ($H^+$) provided by the acidic substance can combine with the tungstate ions to form tungstic acid ($H_2WO_4$). The pH value of the $WO_3$ precursor solution can range from 0 to 6. As such, the $WO_3$ particles formed from the $WO_3$ precursor solution can have an enhanced gas response. Preferably, the pH value of the $WO_3$ precursor solution can range from 0.4 to 2. The acidic substance can be hydrochloric acid (HCl) aqueous solution. However, the present disclosure is not limited thereto. Acidic substances which do not react with the silicon substrate and tungstic acid can be used as the acidic substance of Step 420. Moreover, the $WO_3$ precursor solution is for forming $WO_3$ particles in the hydrothermal synthesis step. Therefore, the method 400 for preparing the $WO_3$ precursor solution is only exemplary, and the present disclosure is not limited thereto. $WO_3$ precursor solutions which can react to form the $WO_3$ particles in the hydrothermal synthesis step are all within the scope of the present disclosure.

Referring back to FIG. 1, in Step 130, a hydrothermal synthesis step is conducted, wherein the $WO_3$ precursor solution is reacted to form a plurality of $WO_3$ particles on the microstructures, so as to obtain the $WO_3$/Si nanocomposite structure. Referring back to FIG. 2, in the $WO_3$/Si nanocomposite structure 200, the $WO_3$ particles 220 are distributed on the plurality of microstructures 212. A particle size D of each of the $WO_3$ particles 220 can range from 5 nm to 100 nm. As such, the $WO_3$ particles 220 show excellent gas response.

According to one embodiment, the hydrothermal synthesis step can be conducted in a heating device, and can include a heating stage, a temperature holding stage and a cooling stage. In the heating stage, the heating device is heated to a predetermined temperature with a predetermined rate. In the temperature holding stage, the heating device is maintained at the predetermined temperature for a predetermined period. In the cooling stage, the heating device is cooled from the predetermined temperature to a room temperature. According to one embodiment of the present disclosure, the heating device can be an autoclave, and the silicon substrate and the $WO_3$ precursor solution are directly disposed in the autoclave. According to another embodiment of the present disclosure, the silicon substrate can be disposed in a clamp device (shown in FIG. 3), and the heating device can be a high temperature furnace. Specifically, after the silicon substrate disposed in the clamp device is dripped with the $WO_3$ precursor solution, the silicon substrate along with the clamp device can be disposed in the high temperature furnace for being heated. The predetermined rate can range from 3° C./min to 10° C./min. The predetermined temperature can range from 140° C. to 250° C. The predetermined period can range from 4 hours to 8 hours. The parameters of the hydrothermal synthesis step can be adjusted according to the type and the size of the microstructures of the silicon substrate, the concentration of the $WO_3$ precursor solution, the desired particle sizes of the $WO_3$ particles, etc.

Please refer to FIG. 1. In Step 140, a drying step is conducted, wherein moisture of the $WO_3$/Si nanocomposite structure is removed. For example, the $WO_3$/Si nanocomposite structure can be taken out from the heating device and placed in an oven and heated at 60° C. for 10 hours. However, the temperature and the time of the drying step can be adjusted according to practical needs, as long as the temperature is not too high to damage the $WO_3$/Si nanocomposite structure and the moisture can be removed.

Please refer to FIG. 1. In Step 150, a plasma modification step is conducted, wherein the surface of the $WO_3$/Si nanocomposite structure is modified by an oxygen-containing plasma. The oxygen-containing plasma refers that the gas source forming the plasma includes oxygen. According to one embodiment of the present disclosure, the $WO_3$/Si nanocomposite structure can be disposed in a plasma cleaning machine, the plasma cleaning machine is vacuumed and an oxygen-containing gas is introduced for forming the oxygen-containing plasma, and the $WO_3$/Si nanocomposite structure is modified by the oxygen-containing plasma for a predetermined time. For example, the plasma cleaning machine can be vacuumed to 0.01 torr. The oxygen-containing gas can be oxygen. The volumetric flow rate of the oxygen introduced into the plasma cleaning machine can be 6 sccm (standard cubic centimeter per minute), the power can be 20 W, and the predetermined time can range from 10 seconds to 120 seconds. Preferably, the predetermined time can range from 40 seconds to 80 seconds. With Step 150, oxygen vacancies on the surface of the $WO_3$/Si nanocomposite structure can be enhanced. When the $WO_3$/Si nanocomposite structure is applied to a gas sensing device, it is favorable for enhancing gas response at room temperature.

<$WO_3$/Si Nanocomposite Structure>

According to the present disclosure, a $WO_3$/Si nanocomposite structure is provided. The $WO_3$/Si nanocomposite structure is manufactured by the method 100.

As shown in FIG. 2, the $WO_3$/Si nanocomposite structure 200 includes a silicon substrate 210 and a plurality of $WO_3$ particles 220. A surface 211 of the silicon substrate 210 is formed with a plurality of microstructures 212. The $WO_3$ particles 220 are distributed on the plurality of microstructures 212. The $WO_3$/Si nanocomposite structure 200 shows response to specific gases, and can be applied to sense the specific gases. Details of the $WO_3$/Si nanocomposite structure 200 can refer to related description above, and the application of the $WO_3$/Si nanocomposite structure 200 for sensing gas can refer to related description below, and are not repeated herein.

<Gas Sensing Device>

According to the present disclosure, a gas sensing device is provided. The gas sensing device includes a $WO_3$/Si nanocomposite structure. Details of the $WO_3$/Si nanocomposite structure can refer to related description above. The $WO_3$/Si nanocomposite structure shows response to specific gases. The specific gases can be but are not limited to $NO_x$, $NH_3$ and acetone vapor. $NO_x$ can be but is not limited to $NO_2$. When the $WO_3$/Si nanocomposite structure is preferably treated with a plasma modification step, the response of the $WO_3$/Si nanocomposite structure to the specific gases at room temperature can be enhanced, and the $WO_3$/Si nanocomposite structure can be applied to sense the specific gases at room temperature. In other words, the gas sensing device can preferably be a room temperature gas sensing device. For example, the $WO_3$/Si nanocomposite structure shows good response to $NO_2$ at room temperature, and thus can be applied to sense $NO_2$ at room temperature.

<Preparation of Examples>

A silicon substrate is provided (Step 110). The manufacturing method of the silicon substrate is as follows. A square piece (2 cm×2 cm) is cut from a p-type silicon wafer follow by being immersing in a first acidic etching solution for 15 seconds and a second acidic etching solution for 1 minute in sequence. The first acidic etching solution is prepared by adding silver nitrate and hydrofluoric acid into deionized water, wherein a concentration of the silver nitrate is 0.01 M, and a concentration of the hydrofluoric acid is 4.6 M. The second acidic etching solution is prepared by adding hydrogen peroxide and hydrofluoric acid into deionized water, wherein a concentration of the hydrogen peroxide is 0.035 M, and a concentration of the hydrofluoric acid is 4.6 M. The reactions of the square piece in the first acidic etching solution are shown in equation (1) to equation (3), and the reactions of the square piece in the second acidic etching solution are shown in equation (4) and equation (5):

$$4Ag^+ + 4e^- \rightarrow 4Ag; \tag{1}$$

$$Si + 2H_2O \rightarrow SiO_2 + 4H^+ + 4e^-; \tag{2}$$

$$SiO_2 + 6HF \rightarrow H_2SiF_6 + 2H_2O; \tag{3}$$

$$H_2O_2 + 2H^+ \rightarrow 2H_2O + 2h^+; \tag{4}$$

$$2H^+ + 2e^- \rightarrow H_2 \uparrow. \tag{5}$$

A $WO_3$ precursor solution is provided (Step 120). The method for preparing the $WO_3$ precursor solution is as follows. A tungstate ion-containing aqueous solution is provided (Step 410), wherein a moderate amount of $Na_2WO_4 \cdot 2H_2O$ and NaCl are dissolved by deionized water to form the tungstate ion-containing aqueous, wherein a concentration of $Na_2WO_4 \cdot 2H_2O$ is 0.02 M, and a concentration of NaCl is 0.04 M. An acidification step is conducted (Step 420), wherein 12 M HCl aqueous solution is dripped into the tungstate ion-containing aqueous solution till the pH value equals to 1.2, so as to obtain the $WO_3$ precursor solution. The reaction of the acidification step is shown in equation (6):

$$WO_4^{2-} + 2H^+ \rightarrow H_2WO_4 \downarrow. \tag{6}$$

The silicon substrate is disposed in a clamp device (reference can be made to FIG. 3). Herein, a glass slide is used as a cover element and a blinder clip is used as a clip element. The $WO_3$ precursor solution is dripped into a gap between two glass slides to contact with the silicon substrate.

The silicon substrate along with the clamp device are disposed in a high temperature furnace, and a hydrothermal synthesis step is conducted (Step 130). First, the high temperature furnace is heated to 150° C. with a rate of 5°

C./min. The high temperature furnace is maintained at 150° C. for 6 hours then stop heating. The high temperature furnace is cooled naturally to room temperature. As such, the $WO_3$/Si nanocomposite structure is obtained.

A drying step is conducted (Step 140). Specifically, the $WO_3$/Si nanocomposite structure is taken out from the high temperature furnace and is separated from the clamp device. The $WO_3$/Si nanocomposite structure is disposed in an oven and heated at 60° C. for 10 hours to remove moisture. The $WO_3$/Si nanocomposite structure treated with the drying step is observed by SEM and is conducted with a gas sensing response test, results thereof are shown as below.

A plasma modification step is conducted (Step 150). The $WO_3$/Si nanocomposite structure is disposed in a plasma cleaning machine (Basic Plasma Cleaner, Harrick Plasma, PDG-32G). The plasma cleaning machine is vacuumed to 0.01 torr, oxygen is introduced into the plasma cleaning machine with a volumetric flow rate of 6 sccm, the power is 20W and the modified time is 60 seconds. Afterwards, the $WO_3$/Si nanocomposite structure is conducted with a gas sensing response test, result thereof is shown as below.

<Property Measurement of Examples>

Figure 5:
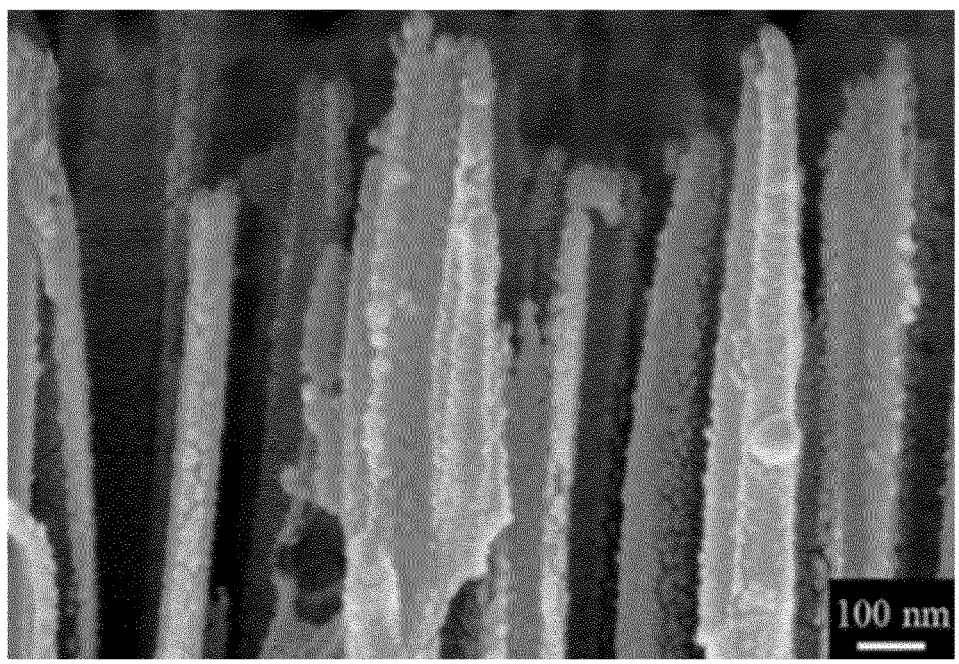
FIG. 5 is a scanning electron microscope (SEM) image of the $WO_3$/Si nanocomposite structure according to one example of the present disclosure.

The $WO_3$/Si nanocomposite structure treated with the drying step is observed by SEM, and the result is shown in FIG. 5. In FIG. 5, the microstructures of the silicon substrate are nanowires, and the $WO_3$ particles are distributed on the microstructures. A particle size of each of the $WO_3$ particles ranges from 5 nm to 100 nm.

Figure 6:
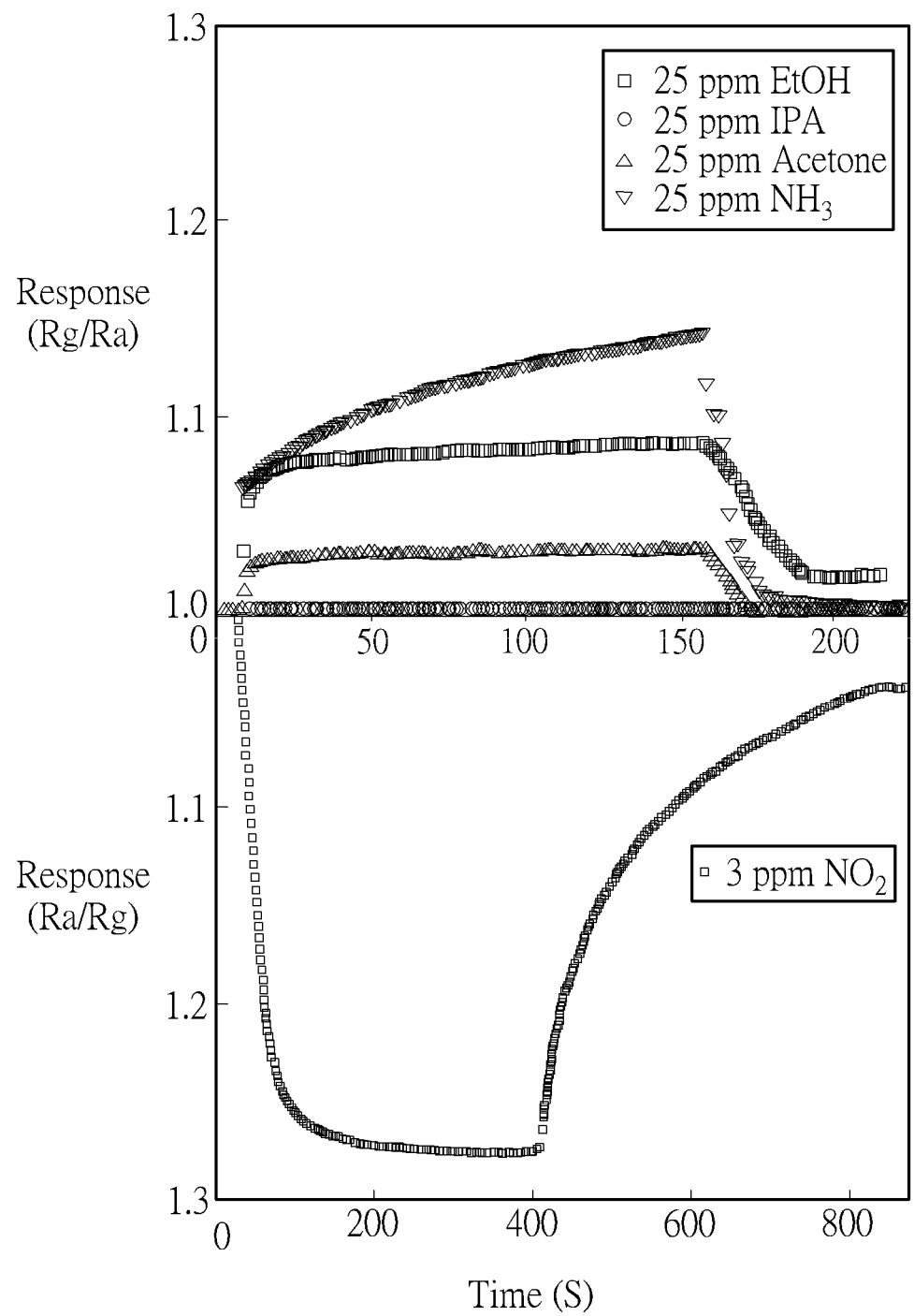
FIG. 6 shows testing result of gas response of the $WO_3$/Si nanocomposite structure at room temperature according to one example of the present disclosure.

The $WO_3$/Si nanocomposite structure treated with the drying step is conducted with the gas sensing response test at room temperature (25° C.), and the result is shown in FIG. 6. Specifically, the responses of the $WO_3$/Si nanocomposite structure to 25 ppm ethanol vapor (EtOH), isopropanol vapor (IPA), acetone vapor and ammonia ($NH_3$) and the response of the $WO_3$/Si nanocomposite structure to 3 ppm nitrogen dioxide ($NO_2$) are measured. As shown in FIG. 6, the response of the $WO_3$/Si nanocomposite structure to 25 ppm isopropanol vapor equals to 1. That is, the $WO_3$/Si nanocomposite structure shows no response to isopropanol vapor. The order of the responses of the $WO_3$/Si nanocomposite structure to the other substances is as follows: $NO_2$>ammonia>ethanol vapor>acetone vapor, wherein the $WO_3$/Si nanocomposite structure shows best response to $NO_2$. Specifically, the test concentration of $NO_2$ is much lower than the other substances, but the $WO_3$/Si nanocomposite structure shows a highest response to $NO_2$.

Figure 7:
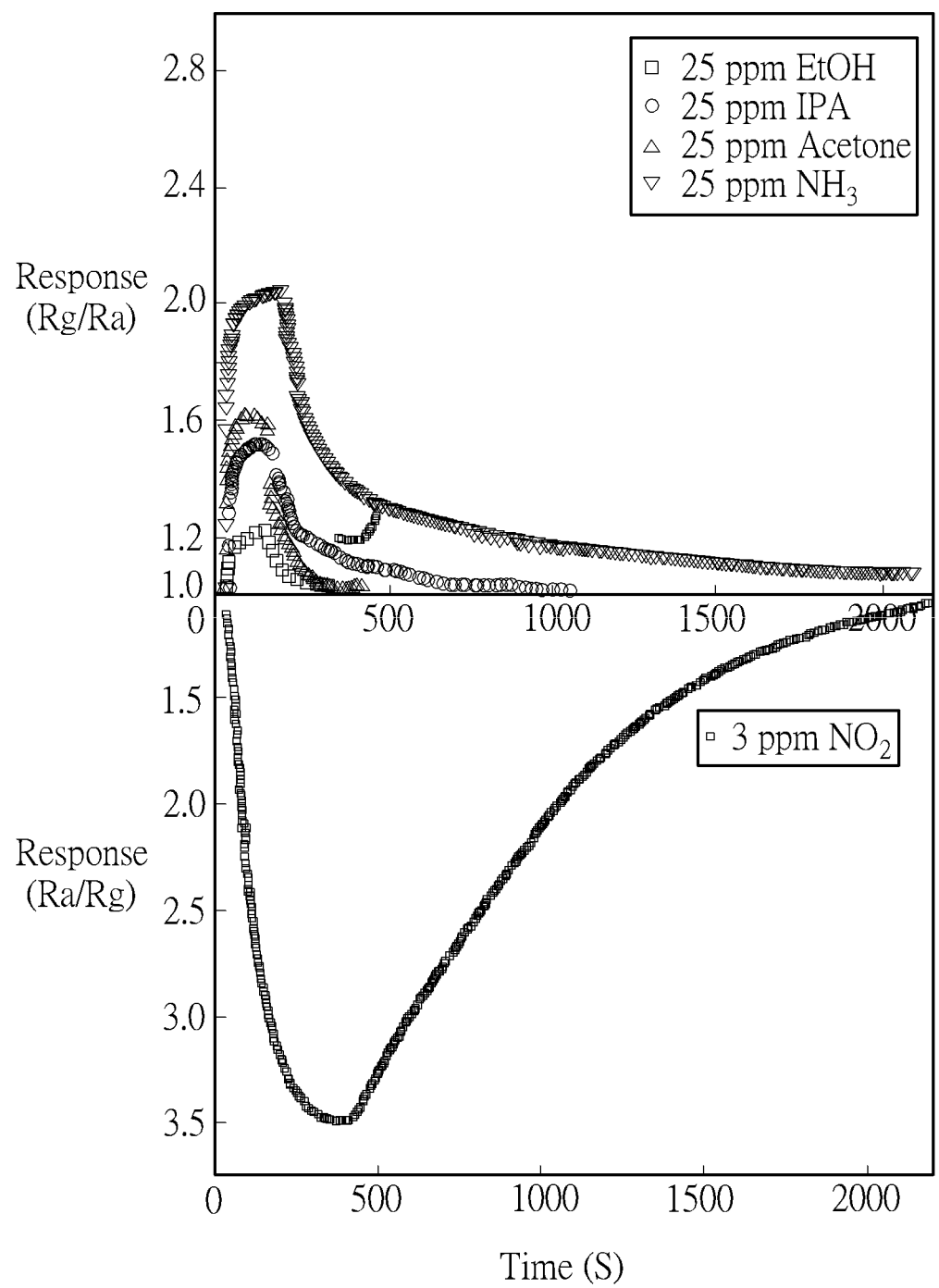
FIG. 7 shows testing result of gas response of the $WO_3$/Si nanocomposite structure at room temperature according to another example of the present disclosure.

The $WO_3$/Si nanocomposite structure treated with the plasma modification step is conducted with the gas sensing response test at room temperature (25° C.), and the result is shown in FIG. 7. As shown in FIG. 6 and FIG. 7, when the $WO_3$/Si nanocomposite structure is treated with the plasma modification step, the responses of the $WO_3$/Si nanocomposite structure to ethanol vapor, isopropanol vapor, acetone vapor, ammonia and $NO_2$ are enhanced significantly. As for isopropanol vapor, the $WO_3$/Si nanocomposite structure changes from non-responsiveness to responsiveness. As for $NO_2$, the response is significantly increased from 1.25 to 3.49.

The $WO_3$/Si nanocomposite structure treated with the plasma modification step is further conducted with a sensing limitation test to $NO_2$. According to the test result, the sensing limitation of the $WO_3$/Si nanocomposite structure to $NO_2$ is 151 ppb. In other words, when the concentration of $NO_2$ in air is extremely low, the $WO_3$/Si nanocomposite structure according to the present disclosure still can sense the existence of $NO_2$.

According to the test results of FIG. 6 and FIG. 7, the $WO_3$/Si nanocomposite structure according to the present disclosure shows response to specific gases, and thus can be applied to sense the specific gases. The response of the $WO_3$/Si nanocomposite structure to the specific gases at room temperature can be enhanced significantly after the $WO_3$/Si nanocomposite structure being treated with the plasma modification step, and thus the $WO_3$/Si nanocomposite structure according to the present disclosure can be applied to room temperature gas sensing device. Furthermore, the $WO_3$/Si nanocomposite structure according to the present disclosure shows excellent response to $NO_2$ and excellent sensing limitation to $NO_2$ at room temperature, and can be applied to sense $NO_2$ at room temperature.

Compared to the prior art, the method for manufacturing the $WO_3$/Si nanocomposite structure according to the present disclosure uses the silicon substrate formed with microstructures as the substrate, which is favorable for enhancing the surface area of the surface where the $WO_3$ particles distributed on. The method for manufacturing the $WO_3$/Si nanocomposite structure according to the present disclosure forms the $WO_3$ particles on the silicon substrate by the hydrothermal synthesis step, which is favorable for reducing the cost when compared to the sputtering method. In the method for manufacturing the $WO_3$/Si nanocomposite structure according to the present disclosure, the silicon substrate can be preferably disposed in the clamp device, and the $WO_3$ precursor solution can be contacted with the silicon substrate by dripping, which can prevent the $WO_3$ particles from agglomerating to form a film in the hydrothermal synthesis step. The method for manufacturing the $WO_3$/Si nanocomposite structure according to the present disclosure can preferably include the plasma modification step, it can increase the oxygen vacancies, which is favorable for enhancing the gas response at room temperature when the $WO_3$/Si nanocomposite structure is applied to the gas sensing device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for manufacturing a tungsten trioxide/silicon nanocomposite structure, comprising:
   providing a silicon substrate, wherein a surface of the silicon substrate is formed with a plurality of microstructures;
   providing a tungsten trioxide precursor solution, wherein the tungsten trioxide precursor solution is contacted with the silicon substrate;
   conducting a hydrothermal synthesis step, wherein the tungsten trioxide precursor solution is reacted to form a plurality of tungsten trioxide particles on the plurality of microstructures, so as to obtain the tungsten trioxide/silicon nanocomposite structure; and
   conducting a plasma modification step, wherein a surface of the tungsten trioxide/silicon nanocomposite structure is modified by an oxygen-containing plasma.

2. The method for manufacturing the tungsten trioxide/silicon nanocomposite structure of claim 1, further comprising:
   conducting a drying step, wherein moisture of the tungsten trioxide/silicon nanocomposite structure is removed.

3. The method for manufacturing the tungsten trioxide/silicon nanocomposite structure of claim 1, wherein each of the microstructures is a nanowire.

4. The method for manufacturing the tungsten trioxide/silicon nanocomposite structure of claim 3, wherein a length of the nanowire ranges from 400 nm to 1400 nm, and a width of the nanowire ranges from 40 nm to 500 nm.

5. The method for manufacturing the tungsten trioxide/silicon nanocomposite structure of claim 1, wherein a method for preparing the tungsten trioxide precursor solution comprises:
   providing a tungstate ion-containing aqueous solution, wherein the tungstate ion-containing aqueous solution comprises tungstate ions and water; and
   conducting an acidification step, wherein an acidic substance is added into the tungstate ion-containing aqueous solution to obtain the tungsten trioxide precursor solution.

6. The method for manufacturing the tungsten trioxide/silicon nanocomposite structure of claim 5, wherein a concentration of the tungstate ions in the tungstate ion-containing aqueous solution ranges from 0.002 M to 1.8 M.

7. The method for manufacturing the tungsten trioxide/silicon nanocomposite structure of claim 5, wherein the tungstate ions are provided by sodium tungstate.

8. The method for manufacturing the tungsten trioxide/silicon nanocomposite structure of claim 5, wherein the tungstate ion-containing aqueous solution further comprises a dispersant.

9. The method for manufacturing the tungsten trioxide/silicon nanocomposite structure of claim 8, wherein a concentration of the dispersant in the tungstate ion-containing aqueous solution ranges from 0.004 M to 0.4 M.

10. The method for manufacturing the tungsten trioxide/silicon nanocomposite structure of claim 8, wherein the dispersant is sodium chloride.

11. The method for manufacturing the tungsten trioxide/silicon nanocomposite structure of claim 1, wherein a pH value of the tungsten trioxide precursor solution ranges from 0 to 6.

12. The method for manufacturing the tungsten trioxide/silicon nanocomposite structure of claim 1, wherein the hydrothermal synthesis step is conducted in a heating device, the hydrothermal synthesis step comprises:
   a heating stage, wherein the heating device is heated to a predetermined temperature with a predetermined rate;
   a temperature holding stage, wherein the heating device is maintained at the predetermined temperature for a predetermined period; and
   a cooling stage, wherein the heating device is cooled from the predetermined temperature to a room temperature.

13. The method for manufacturing the tungsten trioxide/silicon nanocomposite structure of claim 12, wherein the predetermined rate ranges from 3° C./min to 10° C./min, the predetermined temperature ranges from 140° C. to 250° C., and the predetermined period ranges from 4 hours to 8 hours.

14. The method for manufacturing the tungsten trioxide/silicon nanocomposite structure of claim 1, wherein the silicon substrate is disposed in a clamp device, the clamp device comprises two cover elements and a clip element, the silicon substrate is disposed between the two cover elements, and the clip element clamps the two cover elements to fix the silicon substrate between the two cover elements.

15. The method for manufacturing the tungsten trioxide/silicon nanocomposite structure of claim 14, wherein a gap is between the two cover elements, and the tungsten trioxide precursor solution is dripped into the gap to contact with the silicon substrate.

16. A tungsten trioxide/silicon nanocomposite structure, manufactured by the method of claim 1.

17. The trioxide/silicon nanocomposite structure of claim 16, wherein a particle size of each of the tungsten trioxide particles ranges from 5 nm to 100 nm.

18. A gas sensing device, comprising the tungsten trioxide/silicon nanocomposite structure of claim 16.

19. The gas sensing device of claim 18, wherein the gas sensing device is for sensing nitrogen oxides.

* * * * *